United States Patent
Dinsmoor et al.

(10) Patent No.: US 7,571,008 B2
(45) Date of Patent: Aug. 4, 2009

(54) SYSTEM AND APPARATUS FOR REMOTE ACTIVATION OF IMPLANTABLE MEDICAL DEVICES

(75) Inventors: David A. Dinsmoor, St. Paul, MN (US); James K. Carney, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 760 days.

(21) Appl. No.: 10/920,818

(22) Filed: Aug. 17, 2004

(65) Prior Publication Data

US 2005/0043594 A1  Feb. 24, 2005

Related U.S. Application Data

(60) Provisional application No. 60/495,901, filed on Aug. 18, 2003.

(51) Int. Cl.
*A61N 1/00* (2006.01)
(52) U.S. Cl. .......................................................... 607/62
(58) Field of Classification Search ........................ None
See application file for complete search history.

(56) References Cited

U.S. PATENT DOCUMENTS

| | | | | |
|---|---|---|---|---|
| 3,930,142 A | * | 12/1975 | Meier | 377/39 |
| 4,157,087 A | * | 6/1979 | Miller et al. | 600/554 |
| 4,404,972 A | * | 9/1983 | Gordon et al. | 607/16 |
| 5,186,170 A | * | 2/1993 | Varrichio et al. | 607/45 |
| 5,350,412 A | * | 9/1994 | Hoegnelid et al. | 607/34 |
| 5,370,666 A | | 12/1994 | Lindberg et al. | |
| 5,522,865 A | * | 6/1996 | Schulman et al. | 607/56 |
| 5,916,237 A | | 6/1999 | Schu | |
| 5,924,979 A | * | 7/1999 | Swedlow et al. | 600/300 |
| 6,285,897 B1 | | 9/2001 | Kilcoyne et al. | |
| 6,580,947 B1 | | 6/2003 | Thompson | |
| 2002/0068956 A1 | | 6/2002 | Bloemer et al. | |
| 2003/0060858 A1 | | 3/2003 | Kieval et al. | |
| 2003/0149459 A1 | | 8/2003 | Von Arx et al. | |

* cited by examiner

*Primary Examiner*—Scott M Getzow
(74) *Attorney, Agent, or Firm*—Michael C. Soldner

(57) ABSTRACT

An integrated activation system for an implantable medical device (IMD) sharing a power source, the activation system having a switching circuit and a sensing element coupled to the switching circuit. The switching circuit is configured to gate power from the power source to the IMD. The sensing element is configured to draw current from the power source of less than or equal to about 1 nA during inactivation, enable an operation interval of the switching circuit, and trigger a first state change in the switching circuit. The switching circuit further is configured to gate power to the IMD upon receipt of a pre-determined number of signals from the sensing element.

22 Claims, 3 Drawing Sheets

SYSTEM AND APPARATUS FOR REMOTE ACTIVATION OF IMPLANTABLE MEDICAL DEVICES

CROSS-REFERENCE TO RELATED APPLICATION

This application claims the benefit of U.S. Provisional Application No. 60/495,901, filed Aug. 18, 2003.

TECHNICAL FIELD

The present invention relates generally to medical devices, and more particularly to controlling activation of implantable medical devices.

BACKGROUND

Implantable medical devices that are minimally invasive and self-contained are increasingly popular as modes for improving medical care. For example, wireless sensors, leadless stimulators, and drug delivery pumps are some implantable medical devices that are becoming pervasive tools used in medical treatment. Some of these devices are powered by batteries and may operate continuously until the battery is depleted or may intermittently operate with spaced apart "sleep" intervals so as to extend battery longevity.

In designing implantable medical devices, a trade-off is commonly encountered between competing needs for a small device size and for a battery with sufficient capacity to meet longevity goals. The battery is oftentimes the largest component in the implanted medical device and therefore significantly impacts the size of the implantable medical device.

To minimize battery size, it is generally desirable to design a device that draws a negligible amount of current until a deterministic activation occurs. Such design should also be relatively immune to inappropriate activations so as to avoid unnecessary current consumption.

Conventional reed switches have been used in the past with implantable medical devices. For example, a conventional reed switch has been used between the battery and the device circuitry of a pH sensor. As packaged, the reed switch is biased open (i.e., the device is "turned-off") by an external biasing magnet placed over the sensor during manufacture. The pH sensor is "turned-on" just prior to implantation by removing the external biasing magnet.

However, this conventional reed switch generally tends to be too large in size and thus adds significant size to the implant device. Additionally, the reed switch may be susceptible to environmental effects (e.g., magnetic or mechanical) that may result in inappropriate sensor activation. Smaller conventional reed switches, such as micro-electrical mechanical systems (MEMS) reed switches, may not pass sufficient current and are generally not suitable as a drop-in replacement for the conventional reed switch, such as previously described, where higher currents are used. Additionally, MEMS reed switches are generally susceptible to the same environmental effects that may cause inappropriate activation in conventional reed switches.

Other implantable device designs have used monolithic Hall effect sensors, radio frequency (RF) signaling, and ultrasound to activate the device. Monolithic Hall effect sensors have been used in the past to change the state of a device based on a sensed magnetic event. Hall effect sensors typically require a stand-by current and are generally unsuitable as a means for turning a battery-powered device on or off. In implementations utilizing RF signaling, the implanted device "listens" continuously for a unique RF signal. RF signaling shares a similar current consumption characteristic with Hall effect sensors by generally requiring some current to be used while the device is in a stand-by mode. An ultrasound transducer has been used to turn on a switch that subsequently powers a wireless sensor containing a very small battery. In this approach, the ultrasound transducer should be in effective contact with a patient's body to appropriately activate the sensor.

Accordingly, it is desirable to provide an activation device for implantable medical devices that has relatively low or negligible current draw until a deterministic activation occurs. It is also desirable to provide an activation device for implantable medical devices that gates current to the devices while avoiding significant capacity drop to a shared power source and that does not significantly contribute to an overall size of the device. In addition, it is desirable to provide an implantable and minimally invasive medical device having reduced susceptibility to environmental effects that may result in inappropriate activation thereof. Furthermore, other desirable features and characteristics of the present invention will become apparent from the subsequent detailed description of the invention and the appended claims, taken in conjunction with the accompanying drawings and this background of the invention.

BRIEF SUMMARY

According to various exemplary embodiments, a system and apparatus are provided that remotely activate implantable medical devices. In a first exemplary embodiment, an integrated activation system is provided for an implantable medical device (IMD) sharing a power source. The activation system includes a switching circuit and a sensing element coupled to the switching circuit. The switching circuit is configured to gate power from the power source to the IMD. The sensing element is configured to draw current from the power source of less than or equal to about 1 nA during inactivation, enable an operation interval of the switching circuit, and trigger a first state change in the switching circuit. The switching circuit is further configured to gate power to the IMD upon receipt of a pre-determined number of signals from the sensing element.

In a second exemplary embodiment, an integrated activation system is provided for an IMD sharing a power source therewith. The activation system includes a switching circuit and a sensing element coupled to the switching circuit. The switching circuit is configured to gate power from the power source to the IMD, and minimize a voltage drop to the power source while gating power to the IMD. The sensing element is configured to enable an operation interval of the switching circuit, and trigger a first state change in the switching circuit. The switching circuit is further configured to gate power to the IMD upon receipt of a pre-determined number of signals from the sensing element.

In a third exemplary embodiment, an implantable medical apparatus is provided including a power source, an interface integrated circuit (IC) coupled to the power source, a first sensing element coupled to the interface IC, and a medical device coupled to the interface IC. The interface IC includes a counter sub-circuit, a timing sub-circuit configured to establish a first time interval, and a gating element coupled to the counter sub-circuit and the timing sub-circuit. The first sensing element is configured to transmit a first signal to the interface IC upon activation of the first sensing element. The counter sub-circuit is configured to count first sensing element signal transmissions. The gating element is configured to pass current from the power source to the medical device when the counter sub-circuit counts a pre-determined number of first sensing element signal transmissions within the first time interval.

BRIEF DESCRIPTION OF THE DRAWINGS

The foregoing and other aspects and attendant advantages of the invention will become more readily appreciated as the same becomes better understood by reference to the following detailed description, when taken in conjunction with the accompanying drawings, wherein.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary, brief description of the drawings, or the following detailed description.

Figure 1:
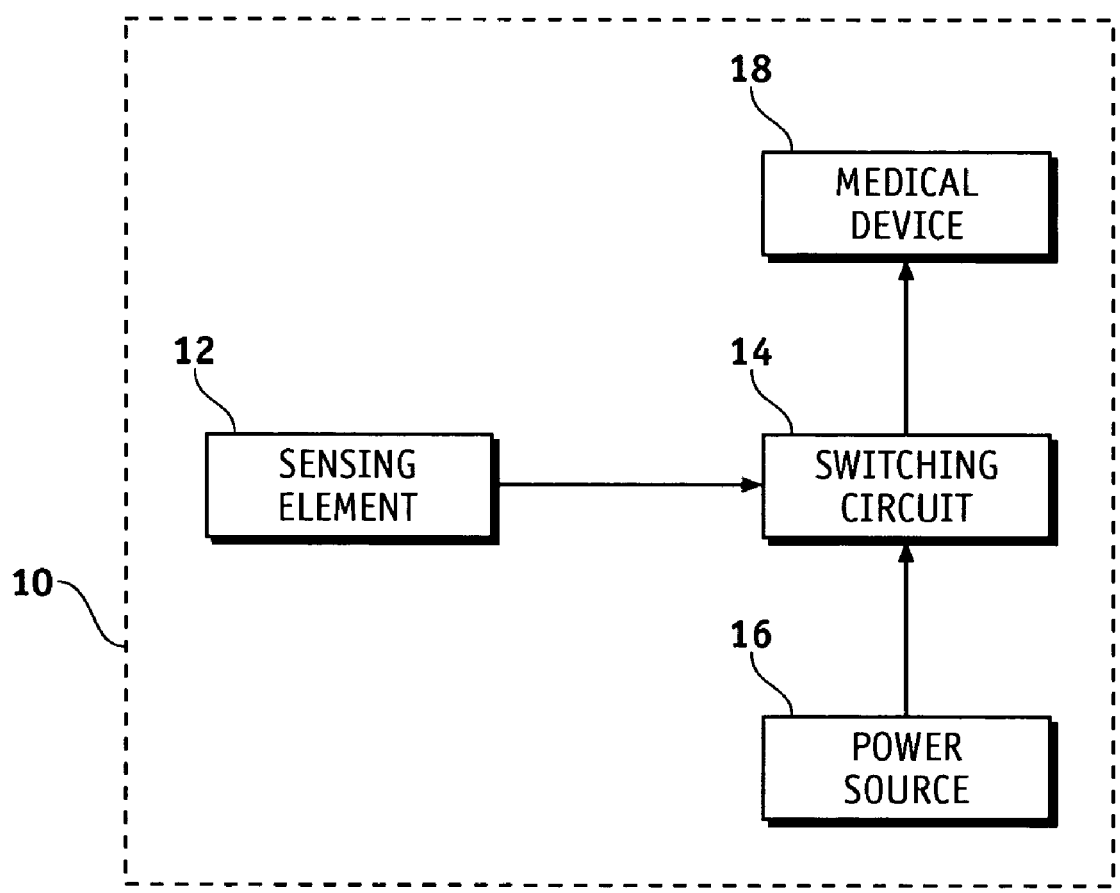
FIG. 1 is a block illustrating an implantable medical device in accordance with an exemplary embodiment of the present invention.

Referring to the drawings, FIG. 1 is a block diagram illustrating an implantable medical device 10 (IMD) in accordance with an exemplary embodiment of the present invention. The IMD 10 includes, but is not limited to, a sensing element 12, a switching circuit 14 coupled to the sensing element 12, and a power source 16 coupled to the switching circuit 14. A medical device 18 may be coupled to the switching circuit 14, such as a wireless sensor, leadless stimulator, drug delivery pump, or any number of implantable medical devices. Although not specifically detailed herein, additional components and circuitry of conventional IMDs may also be included with the IMD 10. The sensing element 12 actuates the switching circuit 14 based on a desired triggering event. For example, if the selected medical device 18 is an implantable probe and the sensing element 12 is a MEMS reed switch, selective application of an external magnetic field by an operator to the sensing element 12 activates the MEMS reed switch 12 which in turn activates the switching circuit 14 to gate power to the implantable probe 18.

The sensing element 12 is configured to detect a change in the environment around the sensing element 12 and is activated upon such detection. Changes detected by the sensing element 12 include, by way of example and not limitation, a physiological change (e.g., blood chemistry pH, body temperature, etc.), a change in a magnetic field, an optical change, or other change in the environment around the IMD 10. Examples of sensing elements 12 include but are not limited to micro-electrical mechanical systems (MEMS) reed switches, thermal bimorphs, photosensors, and the like.

The sensing element 12 may be selected to have a negligible current draw on the power source 16 when inactive, i.e., when not detecting a pre-determined change in the environment around the IMD 10. In one exemplary embodiment, the sensing element 12 has a current draw of equal to or less than about 1 nanoamp (nA) from the power source 16 when inactive. By providing a sensing element that draws relatively small amounts of current or no current from a battery until a deterministic activation occurs reserves as much battery capacity for operation of the IMD 10.

The power source 16 provides current to operate the sensing element 12 during activation of the same. An example of a power source includes, by way of example and not limitation, a battery. The particular current and voltage requirements of the battery 16 may vary depending on the particular medical device 18. Within such current and voltage requirements, the battery size may be selected to minimize the size of the overall IMD 10.

In one exemplary embodiment, when the sensing element 12 is activated, the switching circuit 14 is awakened, and an operation interval, or window, is enabled in the switching circuit 14, such as by a timing circuit described in greater detail hereinbelow. The switching circuit 14 gates power to the medical device 18 to activate the medical device 18 when a pre-determined number or a pre-determined pattern of activations of the sensing element 12 occur within the operation interval.

For example, the switching circuit 14 may be configured to gate power to the medical device 18 after three (3) activations of the MEMS reed switch occur within the operation interval. In this example, activation of the medical device 18, e.g., gating power to the medical device 18, does not occur in the event that the three total activations of the MEMS reed switch occur beyond the operation interval. Configuration of the switching circuit 14 to gate power upon a desired number or pattern of activations of the sensing element 12 is suited to minimizing interference that may occur from the environment. The switching circuit 14 may be configured such that gating power to the medical device 18 occurs on any number or pattern of pre-determined number of activations within the operation interval.

Figure 2:
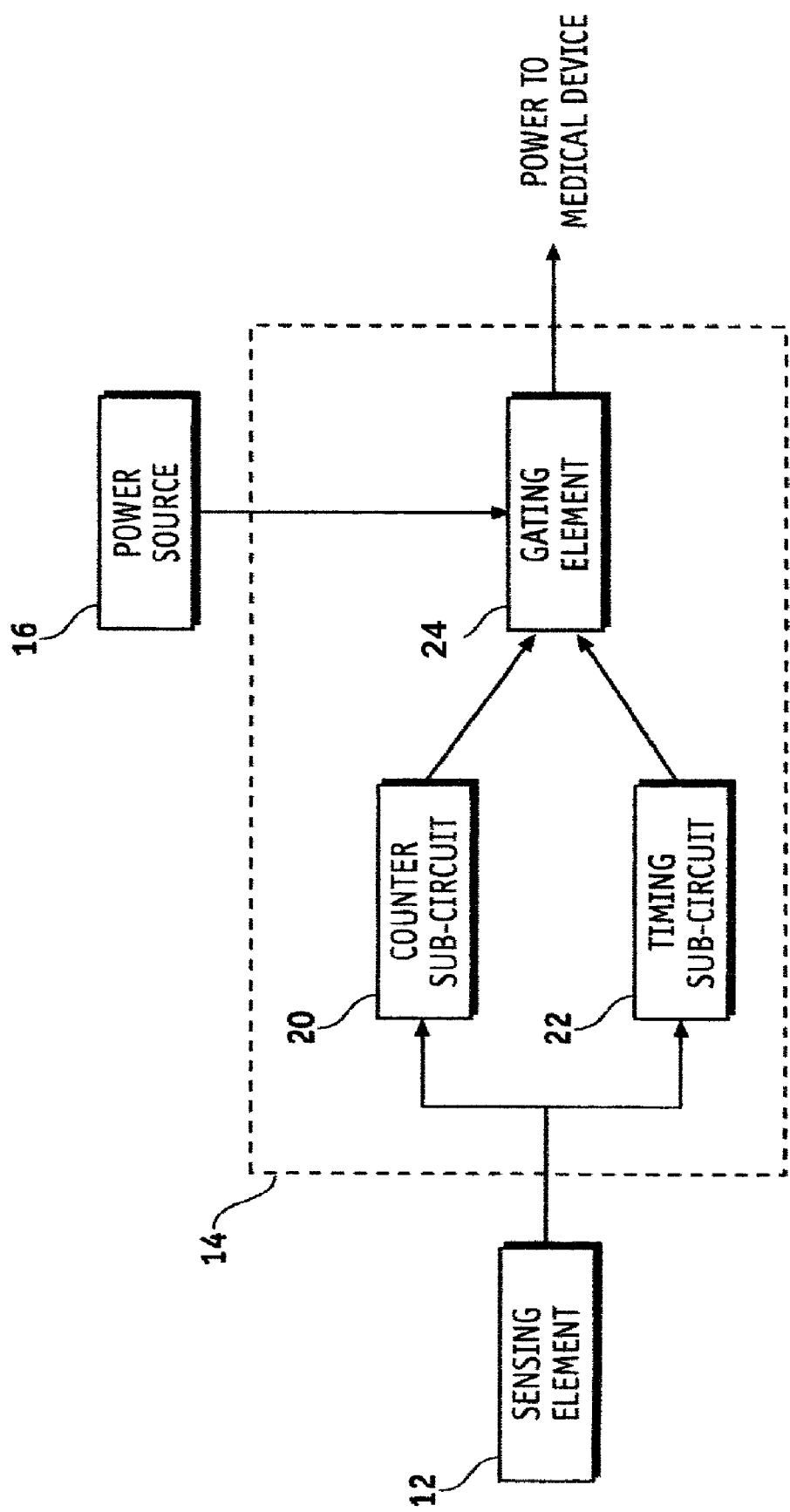
FIG. 2 is a block illustrating one exemplary embodiment of the switching circuit shown in FIG. 1.

FIG. 2 is a block diagram illustrating one exemplary embodiment of the switching circuit 14 shown in FIG. 1. The switching circuit 14 and/or sensing element 12 is selected to minimize any capacity drop of the power source 16 during activation of either to reserve power for gating to the medical device 18 (FIG. 10). The life of the power source 16 may be extended, in comparison with conventional IMDs, by minimizing the capacity drop to the power source 16 that may be result from activation of the switching circuit 14 and/or sensing element 12. In one exemplary embodiment, the switching circuit 14 includes a counter 20, a timer 22, and a gating element 24 coupled to the counter 20 and the timer 22. The switching circuit 14 may be configured as an integrated circuit (IC) such that the counter 20, timer 22, and gating element 24 are incorporated into a monolithic device. The switching circuit 14 or one or more portions thereof, such as the counter 20, timer 22, and gating element 24, may also be configured as embedded instructions or programmable instructions in a microprocessor or a microcontroller contained within or coupled to the IMD 10.

The counter 20 and timer 22 are awakened by activation of the sensing element 12. This initial activation of the sensing element 12 corresponds to a new operation interval or cycle as established by the timer 22. As previously mentioned herein, the switching circuit 14 (FIG. 1) may be configured to gate power to the medical device 18 (FIG. 1). In this exemplary embodiment, the counter 20 may be configured to count a selected or pre-determined number of sensing element 12 activations. The counter 20 may include one or more latches, for example, to count sensing element 12 activations.

As previously mentioned, the timer 22 establishes the operation interval that serves as a basis for the switching circuit 14 to determine whether to gate power to the medical device 18 (FIG. 1). In one exemplary embodiment, the timer 22 includes a resistor and capacitor circuit. The values of the resistor and capacitor determine the length of the operation interval in this embodiment. Although latches are used to describe the counter 20 and a resistor and capacitor combination is used to describe the timer 22, other devices and combinations may also be used. The resulting configuration for the counter 20 and the timer is preferably selected to minimize impact on the overall size of the IMD 10 (FIG. 1).

The gating element 24 controls power gated to the medical device 18 (FIG. 1). This gating is in response to the pre-determined number or pattern of sensing element activations, as determined by the counter 20, occurring within the operation interval established by the timer 22. In one exemplary embodiment, the gating element 24 is a transistor, such as a metal-oxide semiconductor field effect transistor (MOSFET) or a junction type field effect transistor (JFET). The transistor embodiment of the gating element 24 is suited for the monolithic device configuration of the switching circuit 14, although other types of transistors or devices may be also used, such as discrete devices, although not specifically detailed herein.

The switching circuit 14 may additionally include a feedback circuit (not shown) or other feedback mechanism that indicates to the switching circuit 14 when conditions are met for discontinuing gating of power. For example, a second sensing element may be coupled with a feedback circuit that detects for a pre-determined condition, such as a blood pH level. Upon detection of the pre-determined condition, this second sensing element is activated and triggers the feedback circuit. The feedback circuit in turn deactivates the switching circuit 14 to discontinue gating of power to the medical device 18 (FIG. 1).

Additionally, although gating power to the medical device 18 (FIG. 1) is described hereinabove with respect to activation of the sensing element 12, a more robust system for activating the IMD 10 may include one or more conditions to be met prior to gating power. In one exemplary embodiment, another sensing element, e.g., a third sensing element, may be coupled to the switching circuit 14 such that the switching circuit 14 gates power to the medical device 18 (FIG. 1) when both the pre-determined number or pattern of sensing element activations and the third sensing element is activated within the operation interval. For example, the medical device 18 (FIG. 1) receives power from the power source 16 when a MEMS reed switch is activated four times and a detected temperature is about 37° C. within the operation interval.

Figure 3:
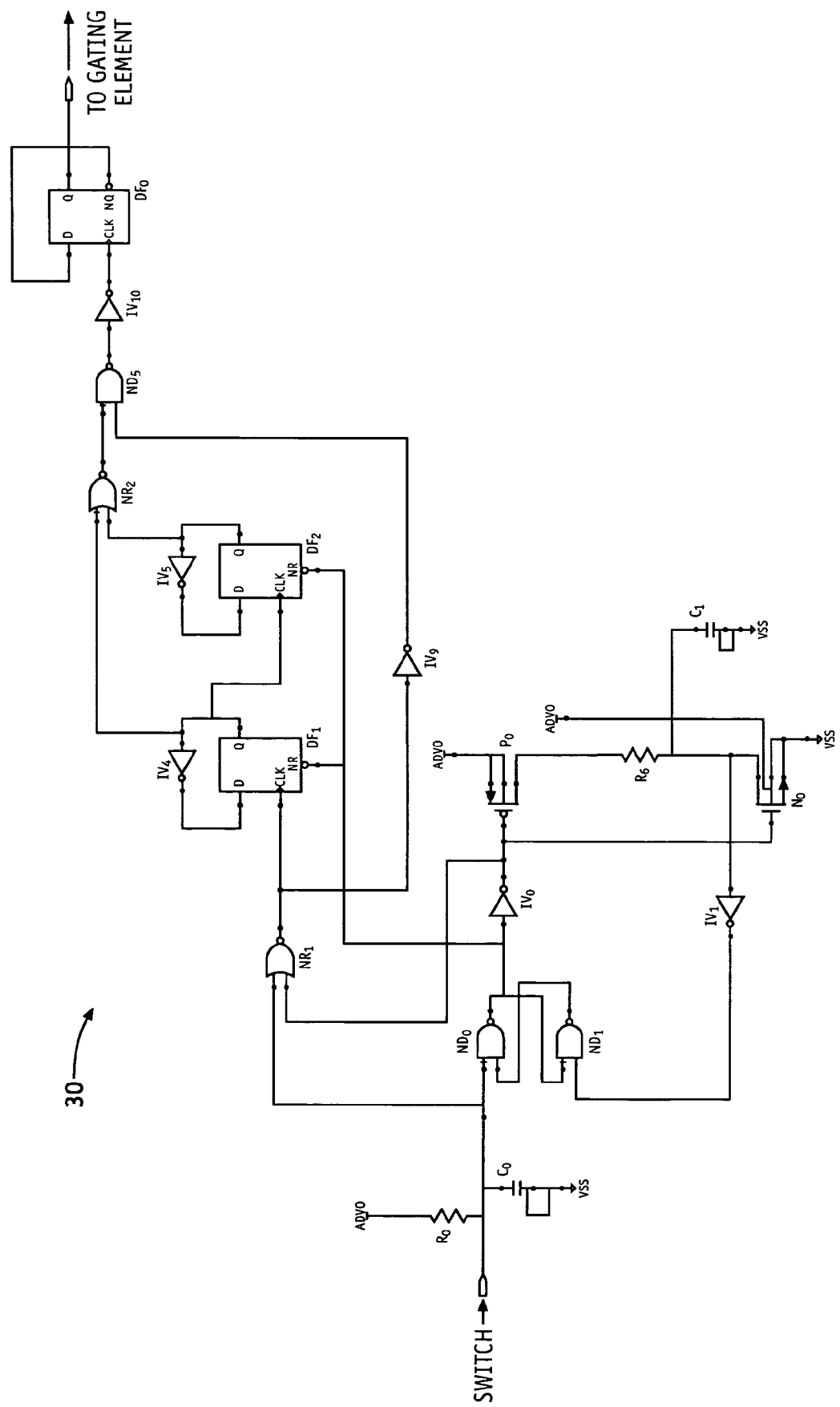
FIG. 3 is a schematic diagram of an exemplary embodiment of a switching circuit.

FIG. 3 is a schematic diagram of an exemplary embodiment of a switching circuit 30. In this exemplary embodiment, one terminal of the sensing element 12 is attached to a node SWITCH. The other terminal of the sensing element 12 may be coupled to ground. The node SWITCH is pulled high through a resistor $R_0$, and a capacitor $C_0$ provides high frequency bypass at the node SWITCH to ground. Logic NAND gates $ND_0$ and $ND_1$ form a reset-set (R-S) latch. The output of $ND_0$ is nominally low to keep a pair of series connected trigger (T) flip-flops $DF_1$ and $DF_2$ in a reset mode and a capacitor $C_1$ discharged to ground. When the output of $ND_0$ is high, such as at startup, an inverter $IV_0$ activates a positive-channel metal-oxide semiconductor (PMOS) $P_0$ and charges the capacitor $C_1$ via a resistor $R_6$. When voltage on $C_1$ reaches a switching point of an inverter $IV_1$, the R-S latch resets and the output of $ND_0$ returns to low.

An resistor/capacitor (RC) element formed by $R_6$ and $C_1$ is used as part of a timing mechanism to toggle the switching circuit 30 on/off. When the sensing element 12 (FIG. 1) activates, a high signal at the output of $ND_0$ sensitizes a logic NOR gate $NR_1$ to signal level changes at the node SWITCH. This sensitivity lasts for an operation interval corresponding to a time for the voltage on $C_1$ to charge to the switch point of $IV_1$. At this point, the R-S latch resets as previously discussed hereinabove. This configuration reduces a likelihood of false state changes in a flop $DF_0$.

Each activation of the sensing element 12 (FIG. 1) while $NR_1$ is sensitized (including the initial activation of the sensing element 12) activates a counter formed by $DF_1$ and $DF_2$ from 11 to 01 to 10 to 00. The switching circuit 30 continuously monitors the output state of the flip-flops $DF_1$ and $DF_2$ at a logic NAND gate $ND_5$. If the output state of the flip-flops is 00 on a rising edge of the node SWITCH, the flop $DF_0$ switches states. The output of $DF_0$ may be buffered to drive a switch that gates current to any additional circuit associated with the IMD 10. Using a falling edge of the node SWITCH to change state in the counter and the rising edge to control $DF_0$ avoids races in the switching circuit 30 as the counter switches state.

In this exemplary embodiment, to gate power to the medical device 18 (FIG. 1) the switching circuit 30 must sense four activations of the sensing element 12 (FIG. 1). If these four activations are not sensed, the potential state change at the output of $DF_0$ is abandoned and the counter resets. Quiescent current consumption in this exemplary embodiment is limited to any leakage current of the devices in the switching circuit 30.

Thus, there has been provided an activation device for implantable medical devices that has relatively low or negligible current draw until a deterministic activation occurs. An activation device for implantable medical devices is also provided that gates current to the devices while avoiding significant capacity drop to a shared power source and that does not significantly contribute to an overall size of the device. Additionally, an implantable and minimally invasive medical device is provided having reduced susceptibility to environmental effects that may result in inappropriate activation thereof.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An integrated activation system for an implantable medical device (IMD), said activation system and said IMD sharing a power source, said activation system comprising:
   a transistor switching circuit configured to gate power from the power source to the IMD; and
   a sensing element coupled to said switching circuit, said sensing element configured to:
   detect a change in a surrounding environment;
   become activated in response to an initial detected change;
   draw current from the power source of less than or equal to about 1 nA during inactivation; and
   enable an operation interval of said switching circuit in response to said initial detected change, said operation interval serving a basis for said switching circuit to determine whether to gate power to the IMD;

said switching circuit further configured to
monitor sensing element signals during said operation interval; and
gate power to the IMD upon receipt of a pre-determined number of sensing element signals within said operation interval.

2. An activation system according to claim 1, wherein said switching circuit is further configured to discontinue gating power to the IMD upon a pre-determined event selected from a pre-determined time period and a second state change.

3. An activation system according to claim 1, wherein said detected change is selected from one of a magnetic field change, an optical change, a thermal change, and a chemical change.

4. An activation system according to claim 1, wherein said sensing element is selected from a micro-electrical mechanical systems (MEMS) reed switch, a thermal bimorph, and a photosensor.

5. An activation system according to claim 1, wherein said sensing element is a MEMS reed switch; and
wherein said switching circuit comprises:
a counter sub-circuit configured to count sensing element activations;
a timing sub-circuit configured to establish said operation interval; and
a gating element coupled to said timing sub-circuit and said counter sub-circuit, said gating element configured to pass current from the power source to the IMD when said counter sub-circuit counts a pre-determined number of sensing element activations within said operation interval.

6. An activation system according to claim 5, wherein said gating element is selected from a transistor and a discrete electronic device.

7. An integrated activation system for an IMD, said activation system and said IMD sharing a power source, said activation system comprising:
a switching circuit configured to:
gate power from the power source to the IMD; and
minimize a voltage drop to the power source while gating power to the IMD; and
a sensing element coupled to said switching circuit, said sensing element configured to:
detect a change in a surrounding environment;
become activated in response to an initial detected change; and
enable an operation interval of said switching circuit in response to said initial detected change, said operation interval serving a basis for said switching circuit to determine whether to gate power to the IMD;
said switching circuit further configured to
monitor sensing element signals during said operation interval; and
gate power to the IMD upon receipt of a pre-determined number of sensing element signals within said operation interval.

8. An implantable medical apparatus comprising:
a power source;
an interface integrated circuit (IC) coupled to said power source, said interface IC comprising:
a counter sub-circuit; and
a timing sub-circuit configured to establish a first time interval;
a gating element coupled to said counter sub-circuit and said timing sub-circuit;
a first sensing element coupled to said interface IC, said first sensing element configured to
detect a change in a surrounding environment;
become activated in response to an initial detected change; and
enable said timing sub-circuit to start the first time interval in response to the initial detected change;
said counter sub-circuit configured to count first sensing element signal transmissions; and
a medical device coupled to said interface IC, said gating element configured to pass current from said power source to power said medical device when said counter sub-circuit counts a pre-determined number of first sensing element signal transmissions within said first time interval.

9. An implantable medical apparatus according to claim 8, wherein said medical device is selected from a drug delivery pump, a stimulator, and a wireless sensor.

10. An implantable medical apparatus according to claim 8, wherein said detected change is selected from one of a magnetic field change, an optical change, a thermal change, and a chemical change.

11. An implantable medical apparatus according to claim 8, wherein said timing sub-circuit comprises a resistor and a capacitor.

12. An implantable medical apparatus according to claim 8, wherein said counter sub-circuit comprises at least one latch device and at least one T flip-flop device.

13. An implantable medical apparatus according to claim 8, wherein said first sensing element is selected from a MEMS reed switch, a thermal bimorph, and an optical detector.

14. An implantable medical apparatus according to claim 8, wherein said first sensing element is further configured to draw a current of less than or equal to about 1 nA during inactivation.

15. An implantable medical apparatus according to claim 14 further comprising a feedback circuit coupled to said interface IC, said feedback circuit configured to detect a pre-determined condition;
wherein said interface IC is further configured to discontinue sourcing current from said power source to said medical device when said feedback circuit detects said pre-determined condition.

16. An implantable medical apparatus according to claim 15, wherein said pre-determined condition is selected from a second time interval, a pH value, and a power source voltage.

17. An implantable medical apparatus according to claim 15, wherein said pre-determined condition is a second time interval; and
wherein said gating element is configured to discontinue sourcing current from said power source to said medical device when said second time interval is detected by said feedback circuit.

18. An implantable medical apparatus according to claim 8 further comprising a second sensing element coupled to said interface IC, said second sensing element configured to transmit a second signal to said interface IC upon detecting a second state change, wherein said gating element is configured to source current from said power source to said medical device when said counter sub-circuit detects said pre-determined number of sensing element signal transmissions within said first time interval and said interface IC receives said second signal.

19. An implantable medical apparatus according to claim 8, wherein said gating element is selected from a transistor integrated with said IC and a discrete electronic device.

20. An implantable medical apparatus according to claim 8, wherein said gating element is a transistor selected from a metal-oxide semiconductor field effect transistor (MOSFET) and a junction type field effect transistor (JFET).

21. An integrated activation system for an implantable medical sensor, comprising:
- a power source providing the sole power source to the sensor;
- a sensor activation circuit coupled between the power source and the sensor and comprising:
  - a transistor switching circuit configured to gate power from the power source to the sensor to toggle the sensor on and off; and
  - a sensing element coupled to said switching circuit, said sensing element configured to
    enable an operation interval of said switching circuit;
  - said switching circuit further configured to
    monitor sensing element signals during said operation interval; and
    gate power to the sensor to turn the sensor on upon receipt of a pre-determined number of sensing element signals within the operation interval.

22. An activation system according to claim 1 wherein enabling the operation interval comprises sensitizing said switching circuit to a sensing element signal, the sensitivity lasting for the operation interval.

* * * * *